United States Patent [19]

Stewart

[11] Patent Number: 4,637,545
[45] Date of Patent: Jan. 20, 1987

[54] WASTE MANAGEMENT SYSTEM

[75] Inventor: Gene L. Stewart, San Diego, Calif.

[73] Assignee: Winfield Corporation, San Diego, Calif.

[21] Appl. No.: 715,638

[22] Filed: Mar. 25, 1985

[51] Int. Cl.$^4$ .............................................. B65D 85/24
[52] U.S. Cl. .................................... 232/43.2; 206/370
[58] Field of Search ........................ 232/43.1, 43.2, 44; 206/370; 220/1 T; 241/99

[56] References Cited

U.S. PATENT DOCUMENTS

| | | | |
|---|---|---|---|
| 3,667,693 | 6/1972 | Leeds et al. | 241/99 |
| 3,750,966 | 8/1973 | Anderson | 241/99 |
| 3,866,861 | 2/1975 | Ratcliff et al. | 232/43.2 X |
| 4,380,316 | 4/1983 | Glinka et al. | 232/43.2 X |

FOREIGN PATENT DOCUMENTS

2103281 2/1983 United Kingdom ............... 232/43.2

Primary Examiner—Robert P. Swiatek
Attorney, Agent, or Firm—Charles H. Schwartz; Ellsworth R. Roston

[57] ABSTRACT

A waste management system, including, a module forming a hollow cover having an open base and with the module including a passageway for receiving medical waste from the exterior to the interior. A disposable container is received within the open base of the module to have the container enclosed by the module. The module is locked in position on a wall mount which fully encloses the disposable container. A key plate is provided for disposition between the locking wall mount and the module to unlock the module from the wall mount and with the key plate locked across the open base of the module in substitution of the wall mount. A cart houses a large waste box and includes an opening into the interior of the cart for providing access to the waste box. The cart includes a cover structure disposed around the opening in the cart and with the cover structure including a cover plate over the opening. The cover structure provides a release of the key plate to allow the cover plate to simultaneously move the key plate away from the opening in the cart while extracting the key plate so as to have the disposable container fall through the opening in the cart into the waste box.

44 Claims, 16 Drawing Figures

WASTE MANAGEMENT SYSTEM

BACKGROUND OF THE INVENTION

1. Field of the Invention

The present invention is directed to a sharps waste management system and specifically to apparatus for receiving, storing and disposing of sharps medical waste. The medical waste may include sharp objects, such as hypodermic needles or disposable hypodermic syringes. The medical waste may include infectious or hazardous material.

2. Description of the Prior Art

The reception, storage and disposal of sharps medical waste is a problem which exists in hospitals and other medical facilities. This waste may take a number of different forms. For example, the types of waste may range from glass vials and microscope slides to scalpels and syringes which are considered both hazardous and infectious. Small amounts of hazardous chemicals may also be contained.

In the prior art, containers have been provided to receive and store the various types of medical waste prior to collection and disposal. For example, semi-rigid containers have been used to receive and store sharp implements such as hypodermic syringes and chemical waste and with these semi-rigid containers being periodically collected for disposal. In general, the reception, storage and disposal of this hazardous/infectious medical waste has been somewhat haphazard since no complete sharps waste management system has been used to organize the reception, storage and disposal of the waste and to thereby maintain a safe orderly handling of the waste.

SUMMARY OF THE INVENTION

The present invention provides for a waste management system including apparatus for receiving, storing and disposing of hazardous medical waste. In particular, the sharps waste management system of the invention includes a plurality of individual modules which may either be portable or wall mounted. Each module encloses a plastic disposable container so that medical waste, such as sharps and chemicals, are received within the container through a passageway in the module. The module, and in particular the disposable container locked within the module, stores the waste in the module prior to collection.

The modules are designed so that the hazardous waste is safely contained within the module. Once the hazardous waste is received and stored within the plastic container supported within the module, the hazardous waste is no longer exposed to medical and housekeeping personnel and access to the waste is thereby eliminated. The module is therefore used to safely receive and store the hazardous/infectious waste prior to collection.

Each module may be portable so that the module can be moved around within a particular hospital area to receive and store the waste. Alternatively, the module may be wall mounted so that the module is locked in a convenient location within the particular hospital area and the waste is then brought to the module to be received and stored. On a periodic basis, the hazardous/infectious waste contained within the plastic container retained by the module is collected. In particular, a specifically designed rolling cart must be used for collecting the disposable containers.

The cart encloses a large compartmentalized waste disposal box for receiving and storing a plurality such as twelve (12) of the disposable plastic containers each of which in turn contains the hazardous/infectious waste. Each module has an open bottom. Mounting the module on the locking wall mount locks the plastic container in position within the module. In order to remove the module from the locking wall mount, a key plate is inserted between the module and the mount. The key plate releases the module from the locking wall mount and acts also as a temporary bottom for the module. The module with the key plate locked in place, covering the bottom, is then brought to the cart for dumping.

The cart includes an opening and with a locked cover structure surrounding the opening. Positioning the module over the cover structure automatically unlocks a slidable cover plate which covers the opening in the cart. In addition, the cover structure includes a portion to release and retain the key plate when a handle is moved so that the key plate may be slid out of the module while at the same time the cover plate is moved away from the opening in the top of the cart to thereby provide access to the large compartmentalized waste box in the interior of the cart. As the key plate and cover plate are slid, the module, retained in the fixed position, is now positioned over the opening to allow the disposable container to fall through the opening into a compartment of the large waste box. The key plate is then removed and the handle slid back so that the cover plate once again covers over the opening through the top of the cart. When the handle and cover plate are moved back to the closed position, a rotating mechanism indexes the divided waste box to the next position. This provides orderly stacking of the disposed containers. A new plastic container is then positioned within the module and the module is once again locked onto the wall mount. If the module is to be portable, then the new plastic container is positioned within the module and a key plate is locked across the bottom of the module.

The sharps waste management system of the present invention therefore provides for a containment of the waste within the module and in particular within the plastic container retained by the module. Exposure of the waste is thereby minimized so as to reduce the hazard to either hospital personnel or patients. When the waste is collected, the plastic container retained by the module is released through an opening normally covered by a sliding cover plate to have the waste collected in a large waste box. The collection of the waste is accomplished without the neccessity of any hospital personnel touching the waste or the plastic container. After all twelve (12) of the modules are emptied, the cart is rolled to a storage area so that the large waste box may be removed from the cart, covered and stored for pickup.

BRIEF DESCRIPTION OF THE DRAWINGS

A clearer understanding of the present invention will be had with reference to the following description and drawings wherein.

DESCRIPTION OF THE PREFERRED EMBODIMENT

Figures 1, 2, 3:
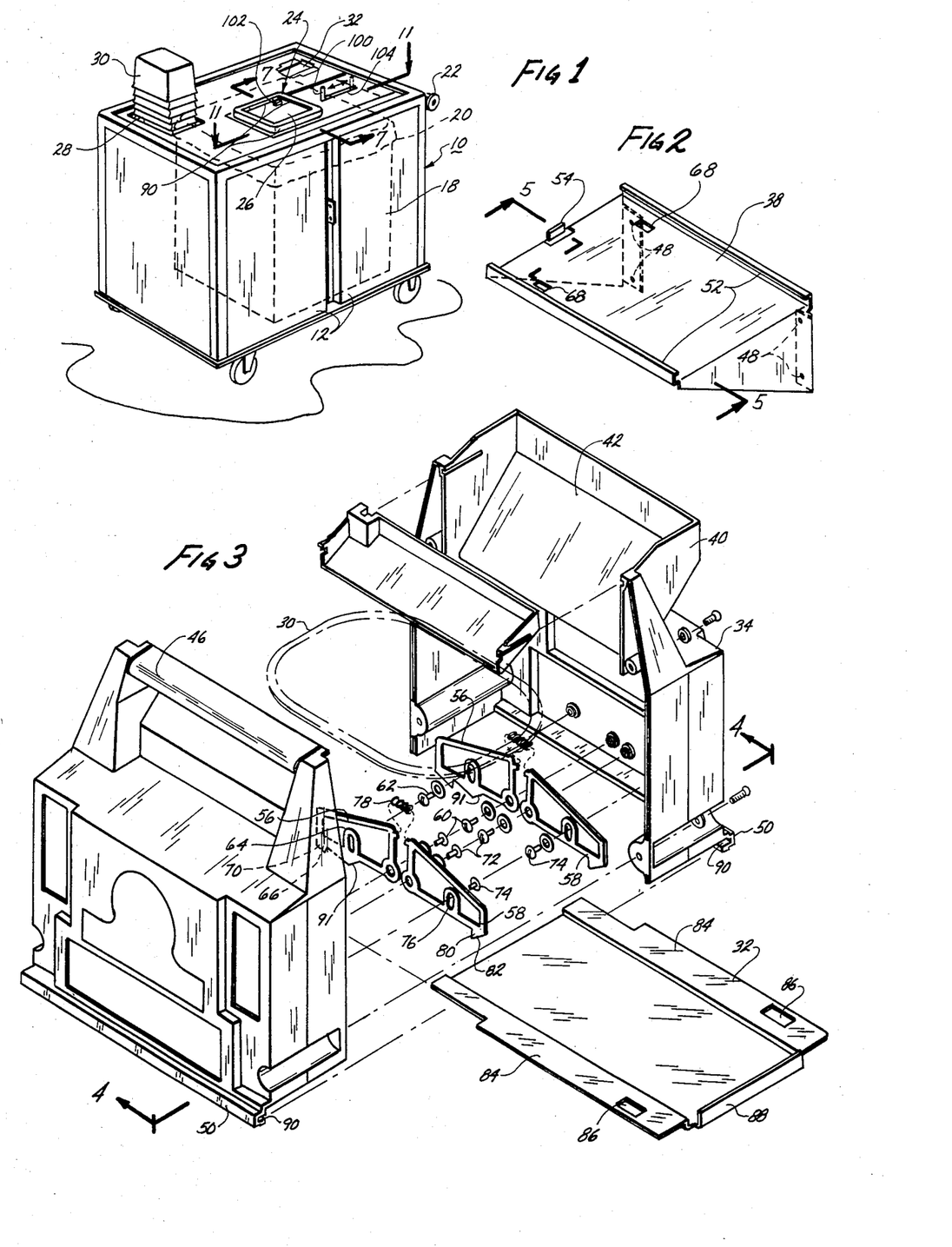
FIG. 1 is an overall view of the waste management cart of the present invention showing the cart with the associated cover structure and with the cart including a large waste box
FIG. 2 is a perspective view of a wall mount for supporting a module.
FIG. 3 is an exploded view of the module retaining a plastic container in position within the module and also showing a key plate for releasing the module from the wall mount and for covering the bottom open end of the module.
Figure 11:
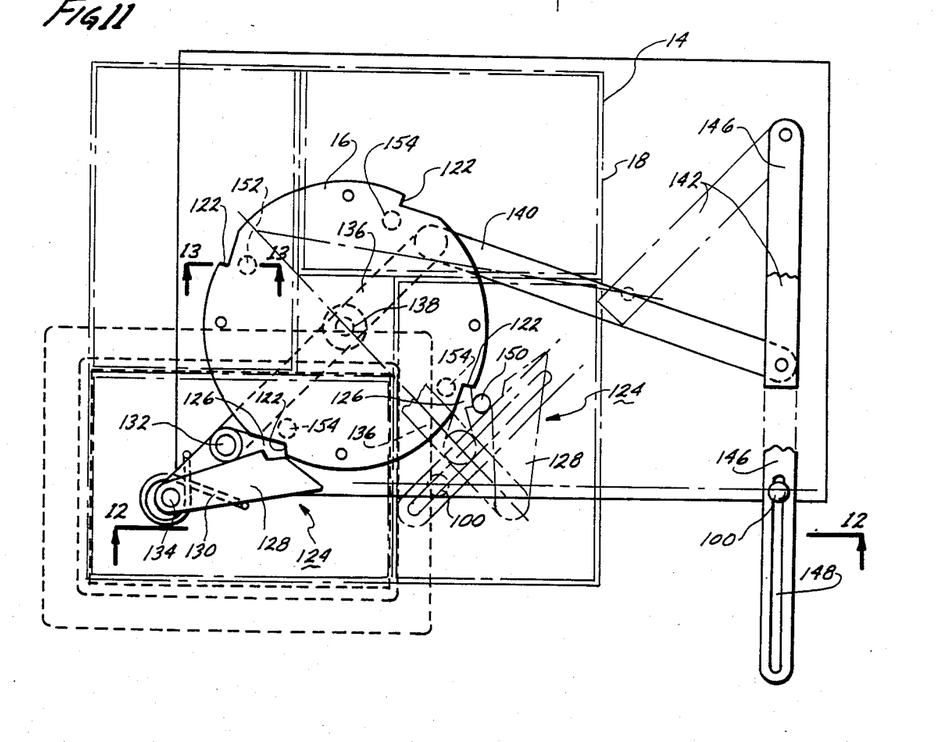
FIG. 11 is a view of the interior of the cart taken along lines 11—11 of FIG. 1 and showing the indexing mechanism for indexing a waste box to a plurality of individual positions.

As can be seen in FIG. 1, the waste management system of the present invention includes a wheeled cart 10 which is used to collect medical waste from a plurality of locations. The cart includes lockable hinged doors 12 which give access to the interior of the cart. A shelf 14 is rotated within the interior of the cart to a plurality of positions by a turntable 16 as seen in FIG. 11. The shelf 14 supports a large waste box 18 which box may be made of cardboard with a plastic liner 20.

The cart 10 may be manuevered by a handle 22 to a plurality of locations such as within a hospital for the collection of medical waste. The waste box 18 would be slid into the interior of the cart 10 and is supported by the rotatable shelf 14 and with the hinged doors closed and locked to prevent any unauthorized access to the interior of the cart. In order to gain access to the interior of the cart, so that the waste box 18 can receive disposable waste, a cover structure 24 including a cover plate 26 is used to surround an opening in the top of the cart. The cover plate 26 covers over the opening in the top of the cart and with the cover structure 24 also including portions to both sides of the cover plate which portions are used to clamp the module in place during the disposal of waste to the waste box located in the interior of the cart.

The top of the cart 10 may also include a recess 28 to store a plurality of extra disposable plastic containers 30. A key plate 32 may be placed in the storage position on the top of the cart which key plate is used during the collection of waste from the plurality of locations.

Figures 4, 5, 13:
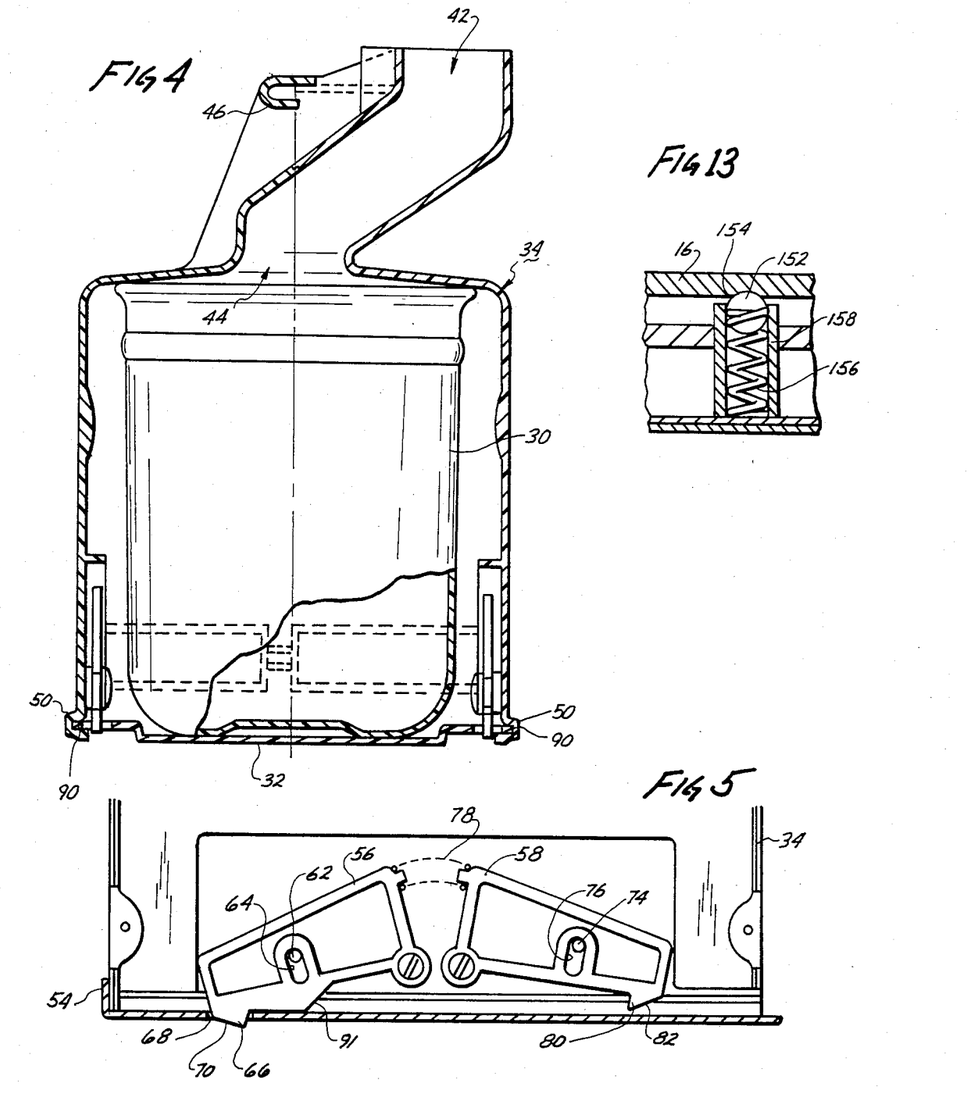
FIG. 4 is a side cross sectional view of the module containing the plastic container and with the key plate in position across the bottom of the module to retain the plastic container.
FIG. 5 is a front cross sectional and partially broken away view of the module showing how the module is locked to the wall mount.
FIG. 13 is a detail view of a detent used in indexing the waste box to the plurality of positions.

In particular, at each of the locations where waste is to be collected, a module 34 is located. As shown in FIGS. 3 and 4, the module 34 is formed with a large open end as a cover to house one of the plastic containers 30. The plastic container 30 is retained in position within the module 34 by a wall mount 38, shown in FIG. 2, forming a locking plate located across the open end of the module or by a key plate 32, shown in FIGS. 3 and 4. The module 34, with its associated key plate 32, may be portable so that the module may be moved about within a specific area. Alternatively, the locking plate may be wall mounted, such as with the wall mount 38, so that the module 34 is retained in a fixed position. In either case, the module 34 is used to receive waste material such as sharp instruments and chemicals from a desired medical area and with the cart 10 wheeled around to a plurality of these different medical areas to retrieve the waste which is received and stored within the module 34.

The module 34 is formed in two parts and includes an upwardly extending four-sided flange portion 40 which is slanted to one side to form an open passageway 42 to receive waste materials. This passageway 42 slants downward through the top of the module to form a throat portion 44 immediately above the disposable container 30. It can be seen therefore, that any waste material dropped into the passageway 42 will slide downward through the throat portion 44 and fall into the disposable container 30. One portion of the upwardly extending flange 40, and specifically the portion 46, additionally serves as a handle to transport the module to the cart 10. When at the cart, the present invention provides for the removal and disposal of the plastic container 30 into the waste box 18 when such module is emptied at periodic times.

As shown in FIG. 5, the module 34 is shown secured to the wall bracket 38 so that the wall bracket serves as a locking plate across the open end of the module. Specifically, as shown in FIG. 2, the wall bracket 38 may include a plurality of openings 48 to receive screw members to secure the bracket to the wall. The wall bracket 38 may therefore be permanently fixed to the wall to thereby retain the module at the fixed location on the wall. Alternatively, the key plate 32 may be locked in position on the bottom of the module 34 without mounting to the wall and with the module 34 therefore being portable for movement within a medical area.

As shown in FIGS. 3 and 4, the module 34 includes flanges 50 extending outwardly at a bottom position. As shown in FIG. 2, the wall bracket 38 includes complementary grooved side portions 52 which are designed to receive and support the flange members 50 so that the wall bracket 38 closes off the open end and forms a locking bottom plate for the module 34. The wall bracket 38 is open at one end and has a small wall portion 54 at the other end. This insures that the module 34 can only be slid into the wall bracket from the open end. This can be seen with reference to FIGS. 2 and 5.

As shown in FIG. 5, the module 34 also includes a pair of pivotable locking detents 56 and 58. As can be seen in FIG. 3, two sets of these pairs of pivotable detents are located on either side of the module 34. As shown in FIG. 5, the locking detent 56 pivots about and is affixed to a pivot pin 60 and with a guide pin 62 maintained within a slot 64 in the detent 56.

A locking portion 66 extends downwardly and is received within an opening 68 in the wall bracket 38. The locking portion 66 includes a ramp 70 so that when the module 34 is inserted into the wall bracket 38, the open end of the locking plate pushes against the ramp surface 70 to pivot the detent 56 upward to allow the module 34 to slide completely into the locking plate until the locking portion 66 falls downward into the opening 68. At this time, the module 34 cannot be removed from the wall bracket since, any attempt to remove the module would provide for the locking portion 66 abutting against the end of the opening 68.

The module 34 also includes the detent 58 which is both pivoted about and secured by the pivot pin 72. A guide pin member 74 is retained within an opening 76 so that the detent 58 may pivot up and down as controlled by the guide pin 74 within the slot 76. A spring member 78 is positioned between the detents 56 and 58 so as to provide positive pressure to maintain the detents 56 and 58 normally in the downward direction. The detent 58 also includes a locking portion 80 having a ramp surface 82.

In order to remove the module 34 from the wall bracket, a key plate 32 is used. The key plate 32 or a similar structure may also serve as a bottom plate when the module is to be used in a portable fashion. As can be seen in FIG. 3, the key plate 32 is formed as a flat plate having upstanding flanges 84 on each side and with each flange including an opening 86. One end of the plate 32 is open and the other end has an upstanding wall 88 so that the key plate can only be inserted in one direction.

Figure 6:
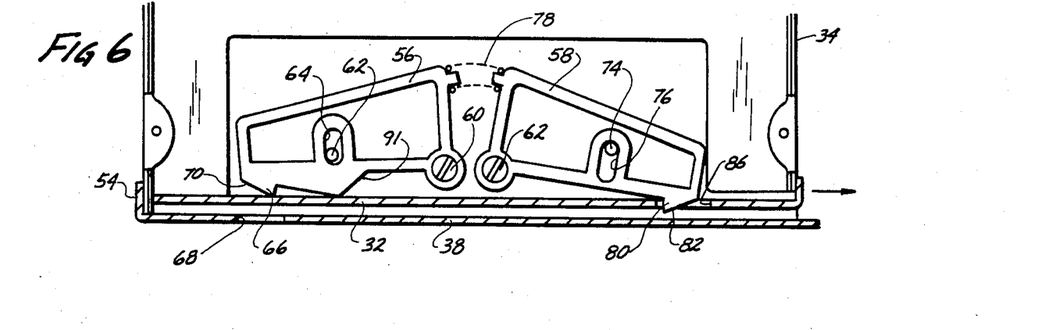
FIG. 6 illustrates the key plate inserted to release the wall mount and with the key plate locked in position to retain the plastic container within the module.
Figure 7:
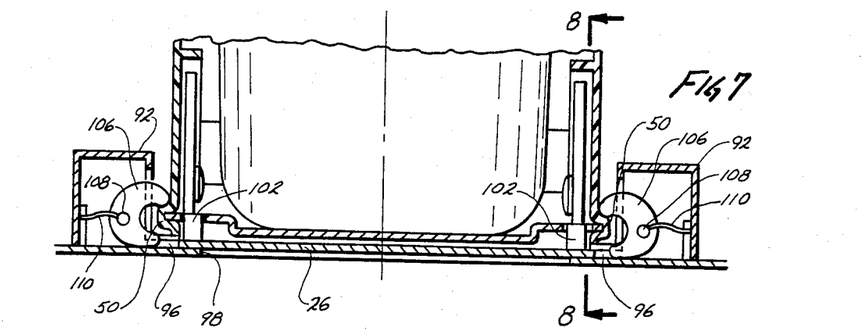
FIG. 7 is a cross-sectional view of a cover structure located at the top of the cart taken along lines 7—7 of FIG. 1 and with the cover structure including a spring loaded clamping means to lock the module within the cover structure.
Figure 8:
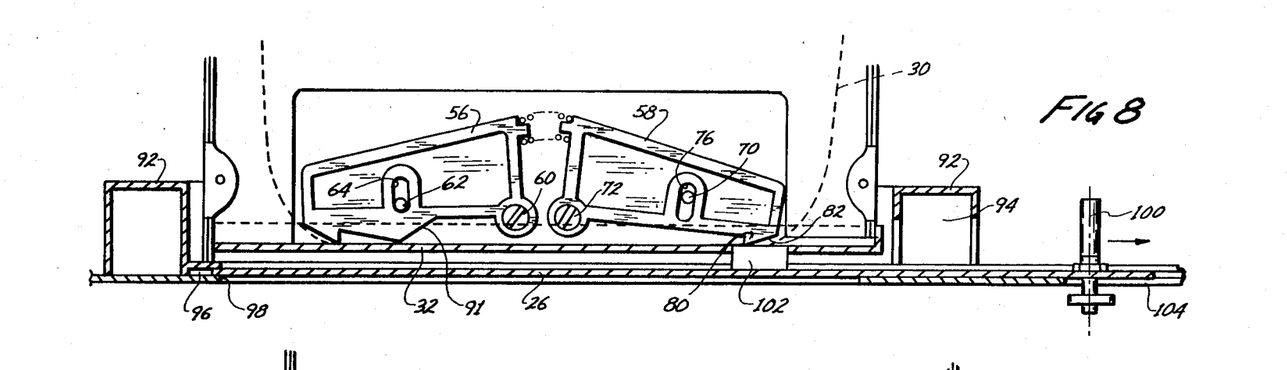
FIG. 8 is a cross-sectional view of the cover structure taken along lines 8—8 of FIG. 7 and with the key plate positioned on a portion of the cover structure so as to release the key plate.

As shown in FIG. 6, the key plate 32 is inserted in the open end of the wall bracket 38 and specifically is inserted at the end of the locking plate opposite the end wall portion 54. The key plate is inserted into slots 90 in the module 34 which slots are shown in FIGS. 3 and 4, and each slot is formed as an inner groove in each of the outwardly extending flange portions 50. The key plate 32 enters between the wall bracket 38 and the bottom of the plastic container 30 and the key plate displaces the container 30 slightly upward.

As the key plate 32 is slid inwardly, the front edge of the key plate contacts the ramp surface 82 to displace the detent 58 in an upward direction. Further insertion of the key 32 provides for the front edge of the key plate contacting a second ramp surface 91 on the detent 56, so that the detent 56 is pivoted upwardly and out of engagement with the wall bracket 38. As the key plate 32 is slid completely into position, the detent 58 drops downward and the locking portion 80 enters the slot 86 in the key plate. The detent 56 is maintained in the upward position as shown in FIG. 6.

The module 34 together with the key plate 32 may now be slid off the wall bracket 38 so that the module is now portable and may now be carried over to the cart 10 so that the disposable plastic container may be dispensed into the waste box 18. In order for the disposable container 30 to be released from the module 34, the key plate 32 has to be removed and at the same time the cover plate 26 in the cover structure 24 has to be slid back. This is all accomplished simultaneously using an interrelationship between the cover structure 24, the key plate 32 and the module 34.

Turning first to FIGS. 1 and 8 to 10, the cover structure is shown to be a recess formed by upstanding walls 92 and with a portion of one of the walls 92 being removed as shown by opening 94. The cover plate 26 is a flat member and is retained within grooves 96 formed in a lower portion of the walls 92 as shown in FIGS. 7 to 10. One end of the cover plate 26 is interconnected with an upstanding arm member 100, which arm member is used to slide the cover plate to expose an opening 98 in the cover structure 24. The arm member 100 is guided by a slot 104 in the top of the cart 10.

Figure 14:
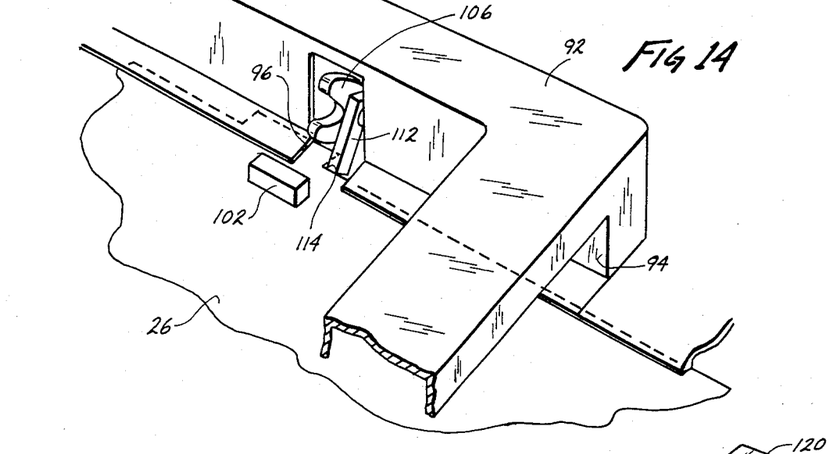
FIG. 14 illustrates a detail of the cover structure showing a locking member to prevent the cover plate from being slid unless a module is positioned within the cover structure.

In operation, the module 34 with the key plate 32 locked across the bottom is positioned in the recessed portion of the cover structure 24. The cover plate 26 includes a pair of upstanding blocks 102. The blocks 102 are designed to release the key plate by passing through the openings 86 in the key plate 32 to engage the locking portions 80 to push the detents 58 upward to thereby release the key plate from the bottom of the module 34. The upstanding walls also include spring loaded clamping members 106 to clamp onto the flanges 50 of the module 34 when the module is pushed downward to release the key plate 32. A plurality of the clamping members 106 are pivotably mounted on pivot pins 108 and with springs 110 providing a spring snap action between an open position shown in FIG. 14 and a closed position shown in FIGS. 7 and 9.

Figure 9:
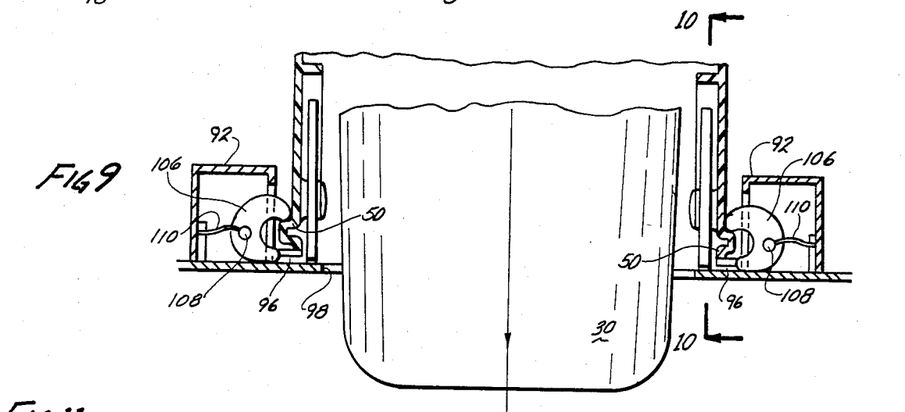
FIG. 9 is a cross-sectional view similar to FIG. 7 and with the plastic container released to fall into the interior of the cart.

The module 34 is thereby pushed downward and clamped in position within the recess formed by the upstanding walls 92. As can be seen in FIG. 9 where the module 34 is clamped in position and the cover plate slid open, this exposes the opening 98 to the interior of the cart so that the container 20 can drop down. When the cover plate 26 is slid back and the module removed, the cover plate is locked in position by a locking arm 12 positioned within a slot 114 in the cover plate 26. The locking arm 112 is pivoted with the clamping member 106 so that when the clamping member is rotated to clamp to the module 34, this also rotates the locking arm 112 out of engagement with the slot 114.

Before the cover plate 26 is slid back so that the cover plate will again cover the opening 98, the key plate 32 is removed. Now when the cover plate is slid back to cover the opening 98, the module has no bottom plate. A new plastic container 30 is inserted into the interior of the module 34 and the module 34 with the container is then reattached to the wall bracket 38. The key plate 32 may be kept loosely on the top surface of the cart for use with a module 34 located in a different area in the hospital. As an alternative, an additional key plate may be used to close off the bottom of the module so that the module may be portable.

Figures 15, 16:
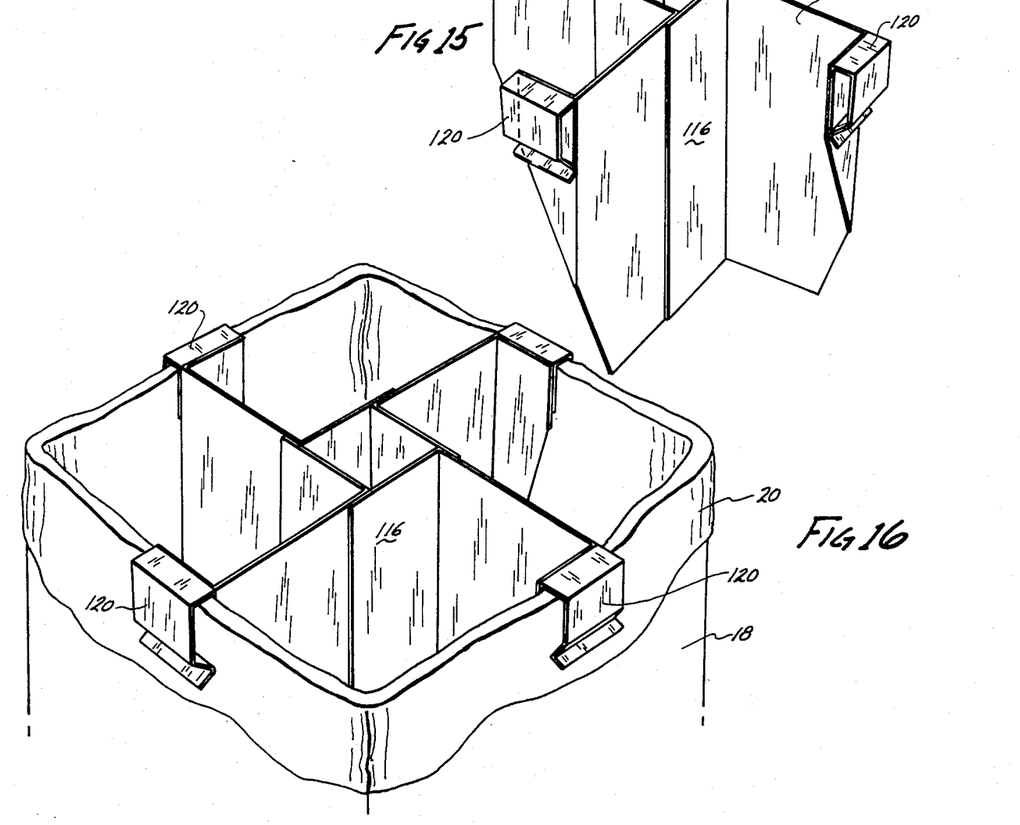
FIG. 15 illustrates a divider member used to compartmentalize the waste box.
FIG. 16 illustrates the divider member within the waste box.

In order to insure that each plastic container 30 falls into the interior of the cart 10 and is received by the waste box 18 in an orderly fashion, the waste box 18 is subdivided into four compartments by a divider member as shown in FIGS. 15 and 16. Specifically, the waste box 18 normally receives a large plastic bag 20 and with a divider member 116 positioned within the plastic bag 20 within the waste box 18. The divider 116 is formed by a plurality of folded sheet metal members 118 welded together to form a center square portion and radiating arm portions. A clip member 120 is attached at the end of each of the radiating arm portions. As can be seen in FIG. 16, when the divider is positioned within the waste box 18, the radiating arm portions subdivide the waste box into four individual compartments and with the clip members 120 clipping onto the outside of the waste box to lock the divider in position. The clips 120 also help to maintain the plastic bag 20 in position.

Each of the four compartments now formed in the waste box 18 is of a size and shape to receive a plurality of plastic containers 30 in a stacked relationship. In particular, as each plastic container falls into one of the compartments in the waste box 18, it is maintained in an upright position. As succeeding containers fall into the same compartment, the individual containers are stacked one above the other. In normal operation, each compartment will receive three such plastic containers 30 so that the waste box 18 as subdivided will receive and contain a total of twelve plastic containers. It is to be appreciated that the divider 116 may be formed from a disposable material, such as cardboard, in place of the sheet metal which is reusable.

In order to insure that the individual compartments in the waste box receive the plastic containers in succeeding order, the waste box is positioned on the rotatable shelf 14 within the cart 10. The shelf is rotated to four different positions by an indexing mechanism turning the turntable 16. This indexing may be seen with reference to FIGS. 11 and 12.

The rotation of the waste box is in conjunction with the opening and closing of the cover structure 24. In particular, each time the cover 26 is opened, a container 30 falls into one of the compartments in the waste box 18. When the cover is then closed, this actuates the indexing mechanism to rotate the turntable 90° so that the next succeeding compartment is now ready to receive the next container 30. This rotation continues each time the cover structure is opened and closed so that the containers 30 are deposited in an orderly progression within the four compartments in the waste box until the box is completely filled.

Figures 10, 12:
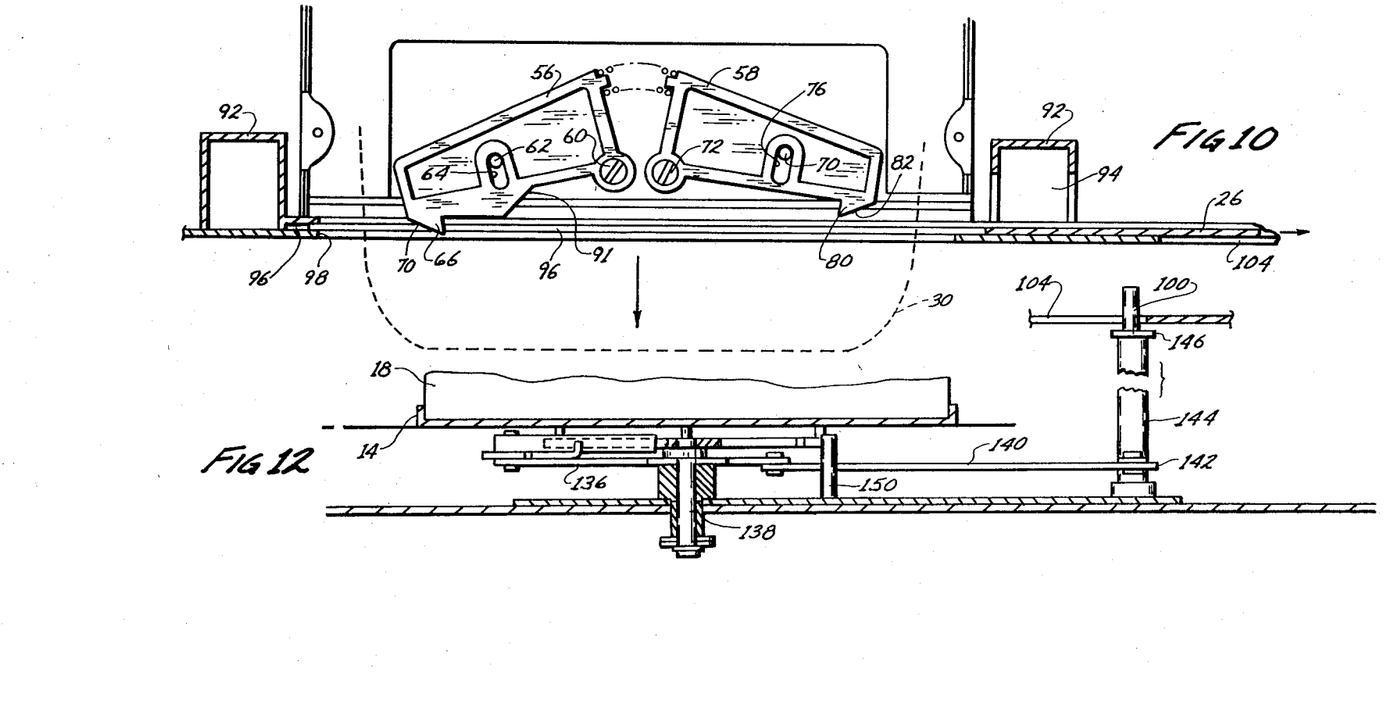
FIG. 10 is a cross-sectional view of the cover structure taken along lines 10—10 of FIG. 9.
FIG. 12 is a cross-sectional view of the indexing mechanism taken along lines 12—12 of FIG. 11.

As can be seen in FIGS. 11 and 12, the turntable 16 forms a ratchet wheel with four ratchet positions 122 located at 90° intervals around the circumference of the turntable. A pawl assembly 124 formed by a pawl member 126 and a locking member 128 is maintained in engagement by a spring member 130. The pawl member 126 is pivoted around a pivot point 132 and the locking member 128 is pivoted around the pivot point 134. The pawl assembly 124 is located at the end of an arm 136 and with the arm pivoted about the same pivot point as the turntable 16. Specifically, both the turntable and the arm 136 pivot around a shaft 138 but are independent of each other.

The turntable assembly also includes additional arm members 140 and 142. Arm member 140 is pivotably linked to arm member 136 and arm member 142 is pivotably linked to arm member 140. As can be seen in FIG. 12, arm member 140 is attached at the bottom portion of a shaft member 144. Extending from the top of the shaft member 144 is an additional arm member 146 which arm member 146 includes a slot 148 to receive the operating handle 100. As the handle 100 is moved between the closed and open positions, the handle provides rotation of the arm member 146 which in turn provides rotation of the shaft 144 which in turn provides rotation of the arm member 142. The arm members 142 and 146 move in unison through the common connection of the rotatable shaft 144. The operation of the handle 100 thereby provides for the operation of the indexing mechanism to rotate the turntable 16.

In particular, the pawl assembly 124 is shown in both full line and dotted positions. In the dotted position, the handle 100 is closed to have the cover plate 26 cover the opening 98 into the interior of the cart. In the dotted position, a pin member 150 separates the pawl member 126 and the locking member 128 so that the pawl assembly may be disengaged from the ratchets 122. In particular, as the handle 100 is moved to open the cover structure, this produces a clock-wise rotation of the arm 136 to have the pawl member 126 slid relative to the ratchet portion 122 of the turntable 16. The pawl assembly thereby rotates clock-wise to the full line position which represents that the handle 100 has been moved all the way to the right to completely open the cover plate 26.

After the container 30 falls into the interior of the cart and into the waste box 18 and after the key plate 32 has been removed, the handle 100 is moved back to close the cover plate 26. At this time, the pawl assembly 124 is locked in position within a ratchet portion 122 and is moved counterclockwise to rotate the turntable 16 ninety degrees (90°). The next compartment of the waste box is now located beneath the cover structure. Each time the cover plate is cycled open and then closed, the waste box is rotated ninety degrees (90°).

In order to insure that the turntable 16 does not rotate when the pawl assembly is moved clock-wise, a detent 152 is used. The detent is shown in greater detail in FIG. 13 and illustrates the detent 152 being formed as a ball member and received in one of four complementary recesses 154 in the turntable 16. The ball member 152 is supported with an upward spring force by a spring member 156 positioned within a sleeve 158.

In operation, the cart 10 is wheeled about to the plurality of locations for the modules 34. At each location, the key plate 32 is used to release the module 34 from the wall bracket 38 and to in substitution, lock the key plate across the bottom of the module. As an alternative, an additional key plate may be used so that the module is portable. The module 34, with the inserted key plate, is then positioned over the cover structure 24 to have the blocks 102 release the key plate so that cover plate 26 may slide back to expose the opening 98 to the interior of the cart 10. The disposable container 30 within the module 34 then falls through the opening 98 to one of the compartments in the waste box 18 within the cart 10.

The key plate 32 is removed and placed on top of the cart and the cover plate is then slid back to have the cover plate 26 once again cover the opening 98. A new plastic container 30 is inserted into the module 34 and the module with its disposable container is then relocked to the locking plate 38. When the cover plate is slid back, the turntable 16 in association with the pawl assembly 24 is rotated ninety degrees (90°) to have the next compartment ready to receive the next plastic container 30.

After the cart has retrieved the medical waste at the plurality of locations, the cart may then be wheeled back to a central location and with the doors 12 unlocked so that the waste box 18 may be removed for later disposal. A new waste box is slid into the interior of the cart so that the cart is now ready for again retreiving waste at a plurality of locations.

It can be seen therefore that the present invention is directed to a sharps waste management system including a module which can be either portable or wall mounted and with a plurality of such modules positioned at strategic locations for the reception and storage of medical waste. The module is formed as an outer cover housing to receive a disposable plastic container and with a locking plate positioned across the bottom of the housing to secure the container within the housing. The system also includes a cart having a cover structure including a cover plate covering an opening into the interior of the cart which interior supports a large waste box. A key plate is used to release the module from the locking plate and with the key plate acting to support the disposable container within the housing while the module is carried to the cart.

The cover structure includes a portion for releasing the key plate to allow the cover plate to be slid away from the opening to allow the disposable plastic container to fall through the opening into the waste box. The key plate is then removed and the cover plate slid back to again cover the opening and also to rotate the waste box to a new position. The cart may also contain a storage space for extra plastic containers so that a new disposable plastic container may be inserted into the module and with the module then relocked to the locking plate.

The module itself includes pivotable detents to allow for the alternate locking to the wall bracket or the key plate. This provides for the sharps medical waste to be stored within the plastic container and retained within the module until the appropriate time when the container is released through the opening in the top of the cart into the waste box.

Although the invention has been described with reference to a particular embodiment, it is to be appreciated that various adaptations and modifications may be made and the invention is only to be limited by the appended claims.

I claim:

1. A waste management system, including,
    a module for forming a hollow cover having a large open end and with the module including a passageway for receiving medical waste from the exterior to the interior,
    a disposable container for reception within the open end of the module to have the container enclosed by the module and with the passageway leading to the disposable container,
    a locking plate positioned across the open end of the module to fully enclose the disposable container,
    a locking means coupled to the module and the locking plate for locking the locking plate across the open end of the module,
    a key plate for disposition between the locking plate and the module for unlocking the locking plate from the open end of the module and with the key plate coupled to the locking means for locking the key plate across the open end of the module in substitution of the locking plate,
    a cart for housing a large waste box and including an opening into the interior of the cart for providing access to the waste box, and
    a cover structure for receiving the module disposed around the opening in the cart and including a cover plate over the opening and with the cover structure including means for providing a release of the key plate to provide for simultaneous movement of the cover plate away from the opening in the cart while extracting the key plate from the open end of the module so as to have the disposable container fall through the opening in the cart into the waste box.

2. The waste management system of claim 1 wherein the passageway from the exterior to the interior of the module is formed by an upstanding flange extending around an opening in the module opposite to the open end of the module.

3. The waste management system of claim 2 wherein the upstanding flange is slanted away from the vertical to provide an offset passageway.

4. The waste management system of claim 2 wherein at least a portion of the upstanding flange is formed as a carrying handle.

5. The waste management system of claim 1 wherein the disposable container is formed of plastic material.

6. The waste management system of claim 1 wherein the locking plate is formed as a wall bracket.

7. The waste management system of claim 1 wherein the locking means includes at least a first detent mounted on the module to lock to a portion of the locking plate.

8. The waste management system of claim 7 wherein the first detent is pivotably mounted on the module and with the first detent including a locking portion extending from the detent to enter into and lock with an opening in the locking plate.

9. The waste management system of claim 7 wherein the locking means includes a second detent mounted on the module to lock to a portion of the key plate.

10. The waste management system of claim 9 wherein the second detent is pivotably mounted on the module and with the second detent including a locking portion extending from the detent to enter into and lock with an opening in the key plate.

11. The waste management system of claim 10 wherein the first detent is pivotably mounted on the module and with the first detent including a locking portion extending from the detent to enter into and lock to the locking plate and with both detents including ramping surfaces for providing pivotable movement of the detents to released positions.

12. The waste management system of claim 1 wherein the opening into the interior of the cart is at a top surface of the cart.

13. The waste management system of claim 1 wherein the cover structure includes a groove to slidably receive and guide the cover plate from a first position covering the opening to a second position exposing the opening and additionally including a handle mounted to the cover plate for moving the cover plate between the first and second position.

14. The waste management system of claim 13 wherein the cover structure includes a plurality of clamping means to clamp the module within the cover structure to hold the module in a fixed position while the key plate is extended and the cover plate moved to expose the opening in the cart.

15. The waste management system of claim 14 wherein the clamping means are snap action rotatable clamps to snap onto and hold the module in position when the module is pressed down on the cover structure while simultaneously unlocking the cover structure.

16. The waste management system of claim 1 wherein the cover structure additionally includes a locking means to permit the cover means from being moved until the module is received by the cover structure.

17. The waste management system of claim 1 wherein the cart includes a storage area for storing additional disposable containers to replace the disposable container which fell through the opening in the cart.

18. The waste management system of claim 1 wherein the cart additionally includes a rotatable platform for supporting the waste box to allow the waste box to be rotated to different positions for more efficient reception of the disposable containers.

19. The waste management system of claim 18 additionally including a divider member for subdividing the waste box into separate compartments for receiving the disposable containers in stacked relationship.

20. The waste management system of claim 19 wherein the platform is indexed to a number of positions corresponding to the number of compartments.

21. The waste management system of claim 20 additionally including an indexing means coupled to the coverplate and the platform for providing for the rotation of the platform each time the cover plate is opened and closed to thereby index the waste box to a new position for each cycle of operation of the cover plate.

22. A waste management system including a movable cart having a waste box for the reception of waste stored in disposable containers, including,
   a module for forming a hollow cover having a large open end and with the module including a passageway for receiving medical waste from the exterior to the interior,
   a disposable container for reception within the open end of the module to have the container enclosed by the module and with the passageway leading to the disposable container,
   a locking plate positioned across the open end of the module to fully enclose the disposable container,
   a locking means coupled to the module and the locking plate for locking the locking plate across the open end of the module, and
   a key plate for disposition between the locking plate and the module for unlocking the locking plate from the open end of the module and with the key plate coupled to the locking means for locking the key plate across the open end of the module in substitution of the locking plate.

23. The waste management system of claim 22 wherein the passageway from the exterior to the interior of the module is formed by an upstanding flange extending around an opening in the module opposite to the open end of the module.

24. The waste management system of claim 23 wherein the upstanding flange is slanted away from the vertical to provide an offset passageway.

25. The waste management system of claim 23 wherein at least a portion of the upstanding flange is formed as a carrying handle.

26. The waste management system of claim 22 wherein the disposable container is formed of plastic material.

27. The waste management system of claim 22 wherein the locking plate includes means for permanently mounting the locking plate to a wall bracket.

28. The waste management system of claim 22 wherein the locking means includes at least a first detent mounted on the module to lock to a portion of the locking plate.

29. The waste management system of claim 28 wherein the first detent is pivotably mounted on the module and with the first detent including a locking portion extending from the detent to enter into and lock with an opening in the locking plate.

30. The waste management system of claim 28 wherein the locking means includes a second detent mounted on the module to lock to a portion of the key plate.

31. The waste management system of claim 30 wherein the second detent is pivotably mounted on the module and with the second detent including a locking portion extending from the detent to enter into and lock with an opening in the key plate.

32. The waste management system of claim 31 wherein the first detent is pivotably mounted on the module and with the first detent including a locking portion extending from the detent to enter into and lock to the locking plate and with both detents including ramping surfaces for providing pivotable movement of the detents to released positions.

33. A waste management system for use with a module forming a hollow cover having a large open end and with the module including a passageway for receiving medical waste from the exterior to the interior and with a disposable container received within the open end of the module to have the container enclosed by the module and with the open end of the module covered by a locking plate or a key plate to fully enclose the disposable container and with the locking plate or key plate locked across the open end of the module, including
   a key plate for disposition between the locking plate and the module when the module includes a locking plate for unlocking the locking plate from the open end of the module and with the key plate coupled to the locking means for locking the key plate across the open end of the module in substitution of the locking plate,
   a cart for housing a large waste box and including an opening into the interior of the cart for providing access to the waste box, and
   a cover structure disposed around the opening in the cart and including a cover plate over the opening and with the cover structure including means for providing a release of the key plate to allow the simultaneous movement of the cover plate away from the opening in the cart while extracting the key plate from the open end of the module so as to have the disposable container fall through the opening in the cart into the waste box.

34. The waste management system of claim 33 wherein the opening into the interior of the cart is at a top surface of the cart.

35. The waste management system of claim 33 wherein the cover structure includes a groove to slidably receive and guide the cover plate from a first position covering the opening to a second position exposing the opening and additionally including a handle coupled to the cover plate for moving the cover plate between the first and second positions.

36. The waste management system of claim 35 wherein the cover structure includes a plurality of clamping means to clamp the module within the cover structure to hold the module in a fixed position while the key plate is extracted and the cover plate moved to expose the opening in the cart.

37. The waste management system of claim 36 wherein the clamping means are snap action rotatable clamps to snap onto and hold the module in position when the module is pressed down on the cover structure.

38. The waste management system of claim 33 wherein the cover structure additionally includes a locking means to permit the cover means from being moved until the module is received by the cover structure.

39. The waste management system of claim 33 wherein the cart includes a storage area for storing additional disposable containers to replace the disposable container which fell through the opening in the cart.

40. The waste management system of claim 33 wherein the cart additionally includes a rotatable platform for supporting the waste box to allow the waste box to be rotated to different positions for more efficient reception of the disposable containers.

41. The waste management system of claim 40 additionally including a divider member for subdividing the waste box into separate compartments for receiving the disposable containers in stacked relationship.

42. The waste management system of claim 41 wherein the platform is indexed to a number of positions corresponding to the number of compartments.

43. The waste management system of claim 42 additionally including an indexing means coupled to the cover plate and the platform for providing for the rotation of the platform each time the cover plate is opened and closed to thereby index the waste box to a new position for each cycle of operation of the cover plate.

44. The waste management system of claim 33 wherein the cart includes a storage area for storing additional disposable containers to replace the disposable container which fell through the opening in the cart.

* * * * *